(12) United States Patent
Meade et al.

(10) Patent No.: US 10,806,599 B2
(45) Date of Patent: Oct. 20, 2020

(54) BONE-CUTTING JIG SYSTEM

(71) Applicant: Allosource, Centennial, CO (US)

(72) Inventors: Denis M. Meade, Littleton, CO (US); Shane Graham, Parker, CO (US); Kyle von Kaenel, Thornton, CO (US)

(73) Assignee: Allosource, Centennial, CO (US)

( * ) Notice: Subject to any disclaimer, the term of this patent is extended or adjusted under 35 U.S.C. 154(b) by 345 days.

(21) Appl. No.: 15/826,324

(22) Filed: Nov. 29, 2017

(65) Prior Publication Data
US 2018/0221174 A1   Aug. 9, 2018

Related U.S. Application Data

(60) Provisional application No. 62/455,804, filed on Feb. 7, 2017.

(51) Int. Cl.
*A61B 17/15* (2006.01)
*A61B 90/00* (2016.01)
(Continued)

(52) U.S. Cl.
CPC ............ *A61F 2/4644* (2013.01); *A61B 17/15* (2013.01); *A61B 17/151* (2013.01); *A61B 2017/00526* (2013.01); *A61B 2017/00969* (2013.01); *A61B 2090/034* (2016.02); *A61B 2090/061* (2016.02); *A61F 2002/4645* (2013.01); *B26D 3/16* (2013.01); *B26D 7/06* (2013.01); *B27B 25/10* (2013.01); *B28D 1/10* (2013.01)

(58) Field of Classification Search
CPC ......... B27B 1/002; B27B 29/02; B27B 25/10; A61F 2/4644; A61B 2090/061; B23D 47/04; B23D 3/16; B28D 1/046; B28D 1/10; B28D 1/06; B28D 1/066; Y10S 33/18; B23B 13/04; B26D 7/0608; B26D 3/167; B26D 3/166; B26D 3/20; B26D 3/161; A22C 17/0033; B25B 1/20; B25B 1/2489
USPC .................. 83/437.2, 466.1, 762, 42; 269/63
See application file for complete search history.

(56) References Cited

U.S. PATENT DOCUMENTS

| 498,262 A | * | 5/1893 | Hemesath | ............. A47J 43/255 241/273.2 |
| 728,424 A | * | 5/1903 | Steffee et al. | ........... B26D 3/16 82/70.1 |

(Continued)

*Primary Examiner* — David W Bates
(74) *Attorney, Agent, or Firm* — James A. Sheridan; Sheridan Law, LLC

(57) ABSTRACT

There is disclosed a system and methods for safely, precisely, and efficiently cutting cadaveric bone segments into a number of dimensionally standardized pieces. One embodiment provides a jig system for use with a band saw. The jig system may include a v-shaped trough riding upon a plate and at least one rail designed to glide within a corresponding groove formed in the band saw table and stretching parallel to the blade. The trough may include a channel having a series of incremental stops extending between its proximal and distal ends. A bone-advancement wedge may be advanced proximally along the channel between the incremental stops to advance at least one bone segment within the trough toward the proximal end of the trough such that, by sliding the rail(s) within the table groove(s), a desired incremental portion of the bone segment is introduced to the blade. Other embodiments are also disclosed.

15 Claims, 9 Drawing Sheets

(51) Int. Cl.
*A61F 2/46* (2006.01)
*A61B 17/00* (2006.01)
*B26D 3/16* (2006.01)
*B26D 7/06* (2006.01)
*B27B 25/10* (2006.01)
*B28D 1/10* (2006.01)

(56) References Cited

U.S. PATENT DOCUMENTS

| | | | | | |
|---|---|---|---|---|---|
| 803,807 | A * | 11/1905 | Burks | ................... | B27B 25/10 83/409 |
| 1,005,128 | A * | 10/1911 | Blain | ................... | B26D 1/547 83/437.2 |
| 1,202,158 | A * | 10/1916 | Caldwell | ................ | B26D 1/547 83/437.2 |
| 1,381,033 | A * | 6/1921 | Thornton | ............. | B23D 51/025 83/762 |
| 1,476,611 | A * | 12/1923 | Hines | ................... | B23B 47/281 408/88 |
| 1,842,573 | A * | 1/1932 | Van Treek | ........... | B23D 51/025 83/762 |
| 1,994,422 | A * | 3/1935 | Sasek | ..................... | B23Q 3/104 269/309 |
| 2,024,111 | A * | 12/1935 | Phillis | ....................... | B25B 1/20 269/87.2 |
| 2,024,112 | A * | 12/1935 | Phillis | ....................... | B25B 1/20 269/87.2 |
| 2,108,992 | A * | 2/1938 | Obenshain | ............ | B26B 29/063 83/762 |
| 2,364,150 | A * | 12/1944 | Lowenstein | ........... | B23Q 3/104 269/203 |
| 2,398,192 | A * | 4/1946 | Scheminger, Jr. | .... | B26B 29/063 83/762 |
| 2,776,683 | A * | 1/1957 | Cowley | ................... | B27B 25/10 269/246 |
| 2,802,267 | A * | 8/1957 | Lackrie | ................... | A47G 19/26 83/875 |
| 2,853,109 | A * | 9/1958 | Norton, Sr. | .......... | B26D 1/0006 83/144 |
| 2,874,688 | A * | 2/1959 | Biesanz, Sr. | .......... | B28D 1/223 125/23.01 |
| 3,379,229 | A * | 4/1968 | Siegal | ................... | B23Q 16/001 30/371 |
| 3,554,244 | A * | 1/1971 | Biscardi | ................. | B27B 25/10 269/56 |
| 3,971,273 | A * | 7/1976 | Peters | ...................... | B26D 1/25 83/42 |
| 4,125,046 | A * | 11/1978 | Kroh | ..................... | B26B 29/063 269/288 |
| 4,131,043 | A * | 12/1978 | Colman | ................ | B26B 29/063 269/902 |
| 4,208,936 | A * | 6/1980 | Whitehouse | ............. | B26D 1/46 83/713 |
| 4,270,426 | A * | 6/1981 | Raphael | ............... | B23Q 1/4866 269/57 |
| 4,465,268 | A * | 8/1984 | Hudson | .................. | B23Q 3/103 269/99 |
| 5,136,909 | A * | 8/1992 | Mellick | ................ | B23D 51/025 269/287 |
| 5,287,784 | A * | 2/1994 | Brockett | ............... | A47J 47/00 83/746 |
| 5,295,896 | A * | 3/1994 | Petersen | ............... | A22B 5/0029 452/135 |
| 5,586,929 | A * | 12/1996 | Butcher | ............... | B23D 47/045 451/213 |
| 5,626,067 | A * | 5/1997 | Lothe | ..................... | B26B 29/06 269/289 R |
| 6,435,497 | B1 * | 8/2002 | Borter | ................... | B23Q 3/104 269/296 |
| 6,458,144 | B1 * | 10/2002 | Morris | ............... | A61B 17/1637 606/179 |
| 6,648,894 | B2 * | 11/2003 | Abdelgany | ........... | A61F 2/4644 606/79 |
| 6,945,858 | B1 * | 9/2005 | Holmes | ................ | B23D 45/146 125/13.01 |
| 6,993,821 | B2 * | 2/2006 | Ahti | ...................... | B23Q 3/103 269/297 |
| 7,011,085 | B1 * | 3/2006 | Lochotzki | ................ | B28D 7/04 125/23.02 |
| 7,159,496 | B2 * | 1/2007 | Maes | .................... | B23D 45/12 269/41 |
| 2004/0097946 | A1 * | 5/2004 | Dietzel | .................. | A61B 17/15 606/79 |
| 2007/0173852 | A1 * | 7/2007 | Gil et al. | ........... | A61B 17/1635 606/87 |
| 2016/0199995 | A1 * | 7/2016 | Becker | ................... | B27B 25/10 83/23 |

* cited by examiner

BONE-CUTTING JIG SYSTEM

REFERENCE TO PENDING PRIOR PATENT APPLICATION

This application claims the benefit under 35 U.S.C. 119 (e) of U.S. Provisional Patent Application No. 62/455,804, filed Feb. 7, 2017 by Denis M. Meade, Shane Graham, and Kyle von Kaenel for "BONE CUTTING JIG SYSTEM," which patent application is hereby incorporated herein by reference.

BACKGROUND

An allograft includes bone, tendon, skin, or other types of tissue that is transplanted from one person to another. Allografts are used in a variety of medical treatments, such as knee replacements, bone grafts, spinal fusions, eye surgery, and skin grafts for the severely burned. Allografts come from voluntarily donated human tissue obtained from cadaveric donor-derived, living-related, or living-unrelated donors and can help patients regain mobility, restore function, enjoy a better quality of life, and even save lives in the case of cardiovascular tissue or skin.

Processing operations for osseous-based allografts often require a technician to precision cut human cadaveric bone into standardized pieces according to predefined specifications and/or dimensions using industrial cutting equipment, such as a band saw. These precision-cutting operations generally occur within FDA-regulated human tissue banks or processing centers during the preparation of osseous-based allografts prior to further processing and later surgical implantation. Because human bone is non-uniform and irregular in size, form, and shape, such cutting processes can be complicated, time-consuming, dangerous for the technician exposed to the blade or abrasive surface, and prone to errors and inconsistencies.

Existing cutting jigs are available for a variety of purposes, including woodworking (e.g., cabinet making), metalworking, and meat-cutting applications. These types of jigs may be helpful in their respective industries, but they are not adapted for use with non-uniform osseous tissues and do not account for the corresponding cleaning, decontamination, and sterilization requirements required by FDA regulations in the human-tissue processing industry to prevent cross contamination between donors.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

One embodiment provides a system for cutting one or more cadaveric bone segments into dimensionally standardized pieces using a cutting apparatus having a cutting surface disposed orthogonally to a table. The system may include a v-shaped trough extending from a proximal end positioned adjacent the cutting surface to a distal end positioned opposite the cutting surface, the v-shaped trough configured to glide along a top surface of the table parallel to the cutting surface, thereby defining a cutting path adjacent the proximal end of the trough, the v-shaped trough forming a number of incremental stops between the proximal end and the distal end. The system may additionally include a bone-advancement wedge comprising a handle coupled to an advancement panel positioned within the v-shaped trough, wherein when the one or more of the cadaveric bone segments are disposed within the v-shaped trough, proximally advancing the bone-advancement wedge to a next one of the number of the incremental stops proximally advances the one or more of the cadaveric bone segments an incremental distance beyond the cutting path.

Another embodiment provides a jig system for cutting at least one bone segment having a proximal end and a distal end into a number of dimensionally standardized pieces. The jig system may include (1) at least one rail configured to glide within a groove formed in a band saw table; (2) a plate attached to a top surface of the at least one rail; (3) a trough attached to a top surface of the plate, the trough having a proximal end disposed adjacent a blade positioned orthogonally to the band saw table, a distal end disposed opposite the blade, first and second longitudinal walls extending between the proximal and the distal ends of the trough, and one or more incremental stops located between the proximal and the distal ends of the trough, the trough configured to receive the at least one bone segment with the proximal end of the at least one bone segment positioned at the proximal end of the trough; and (4) a bone-advancement wedge, comprising: (a) an advancement panel abutting the distal end of the at least one bone segment, the advancement panel configured to advance to each of the one or more of the incremental stops toward the proximal end of the trough; and (b) a handle extending from the advancement panel through the first longitudinal wall of the trough, the handle configured to selectively engage with each of the one or more of the incremental stops, such that when the handle is advanced proximally between the one or more of the incremental stops, the proximal end of the at least one bone segment advances an incremental distance beyond the proximal end of the trough.

Yet another embodiment provides a method of cutting one or more bone segments using (1) a cutting apparatus having a table positioned orthogonally to a cutting surface, and (2) a bone-cutting jig system disposed upon the table adjacent to the cutting surface, the jig system having (a) a v-shaped trough having a proximal end adjacent the cutting surface and a distal end, and (b) a bone-advancement wedge positioned within the v-shaped trough and configured to advance proximally through a number of incremental stops formed between the proximal and the distal ends of the v-shaped trough. The method may include the steps of (i) positioning the one or more of the bone segments within the v-shaped trough such that a proximal end of the one or more of the bone segments protrudes from the proximal end of the v-shaped trough; (ii) positioning the bone-advancement wedge at a select one of the number of the incremental stops such that an advancement panel of the bone-advancement wedge abuts a distal end of the one or more of the bone segments; (iii) gliding the v-shaped trough along the table parallel to the cutting surface such that the cutting surface intersects the one or more of the bone segments along a cutting path formed adjacent the proximal end of the v-shaped trough and a protruding portion of the one or more of the bone segments is cut away; (iv) advancing the bone-advancement wedge proximally to a next one of the number of the incremental stops; and (v) repeating the gliding the v-shaped trough along the table and the advancing the bone-advancement wedge until the one or more of the bone segments are cut into a number of desired dimensionally standardized pieces.

Other embodiments are also disclosed.

Additional objects, advantages and novel features of the technology will be set forth in part in the description which follows, and in part will become more apparent to those skilled in the art upon examination of the following, or may be learned from practice of the technology.

BRIEF DESCRIPTION OF THE DRAWINGS

Non-limiting and non-exhaustive embodiments of the present invention, including the preferred embodiment, are described with reference to the following figures, wherein like reference numerals refer to like parts throughout the various views unless otherwise specified. Illustrative embodiments of the invention are illustrated in the drawings, in which.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments of the systems and methods described herein relate to the safe, efficient, precise, and effective processing of osseous-based allografts using the assistance of a bone-cutting jig system. As discussed above in the Background section, existing tools do not provide a mechanism for safely and efficiently cutting cadaveric bone according to predefined specifications or dimensions. Because osseous-based tissues are non-uniform and inconsistently shaped, and because cutting and preparation activities for osseous-based tissues are subject to stringent FDA regulations regarding equipment cleaning, decontamination, and sterilization, existing tools do not provide an adequate solution for the uniform cutting of bone during allograft preparation.

Currently, technicians preparing osseous-based allografts are required to manually gauge or "eyeball" dimensions during cutting operations. In addition, the technician's hands and fingers must currently be placed adjacent to, in alignment with, and/or in the path of the cutting surface when making perpendicular cuts to osseous tissue. This approach decreases cut accuracy and precision and places the technician at risk for traumatic workplace injury.

Embodiments of a jig cutting system disclosed herein are designed to address the particular challenges presented in the osseous-based allograft industry, with improved cutting efficiency and dimension accuracy, precision, and consistency that also allows the user to avoid the path of the blade and any associated traumatic injuries when preparing osseous-based allografts. Embodiments of the jig cutting system are also designed for regular sterilization following each use as required in the human-tissue processing industry.

Figure 1:
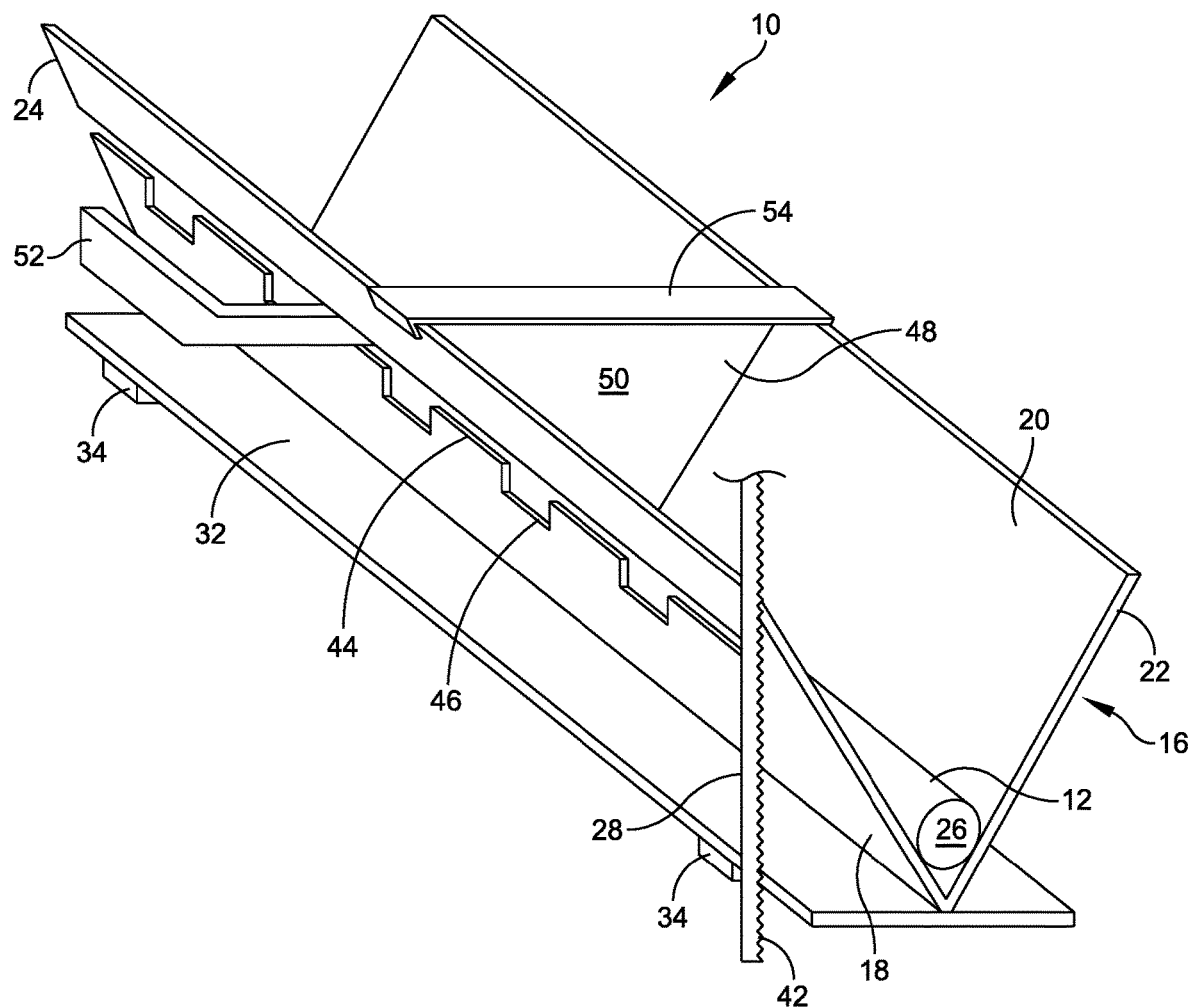
FIG. 1 illustrates a perspective view of one embodiment of a bone-cutting jig system supporting at least one long-bone segment for safely cutting into a number of dimensionally standardized pieces.
Figure 2:
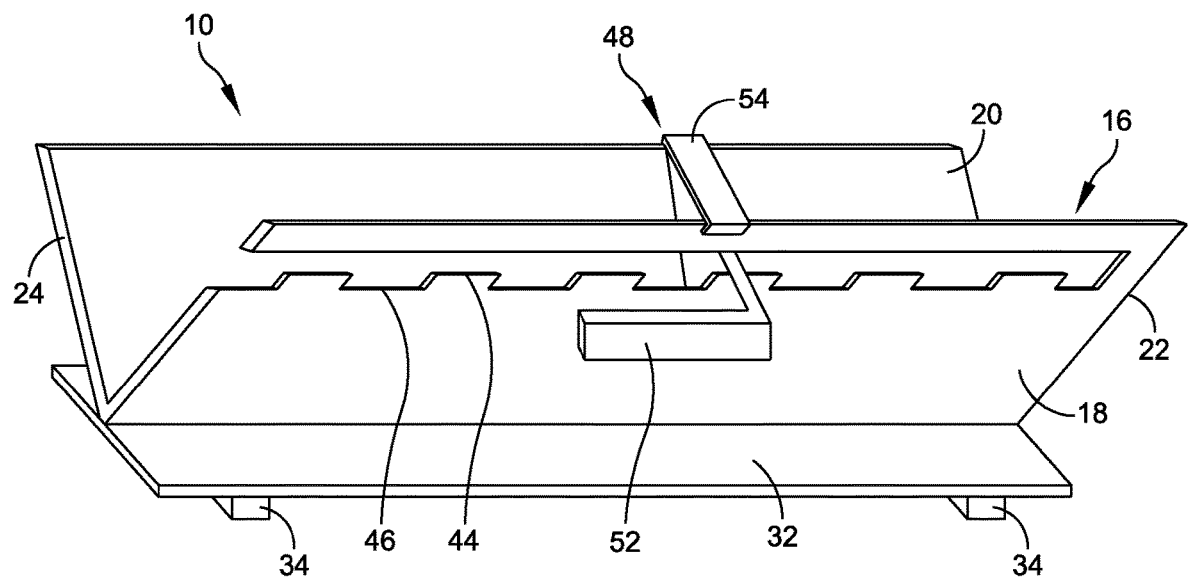
FIG. 2 illustrates a right-side view of the jig system of FIG. 1.
Figure 3:
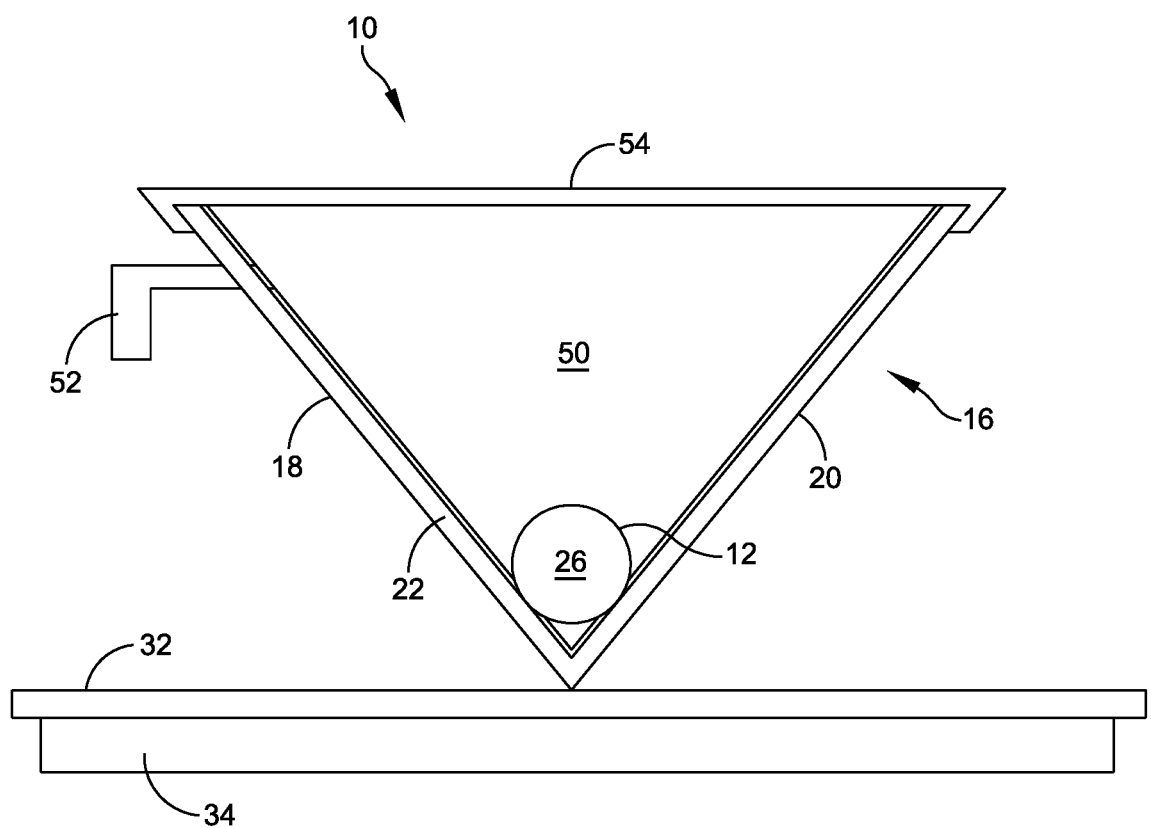
FIG. 3 illustrates a front-end view of the jig system of FIG. 1.
Figure 4:
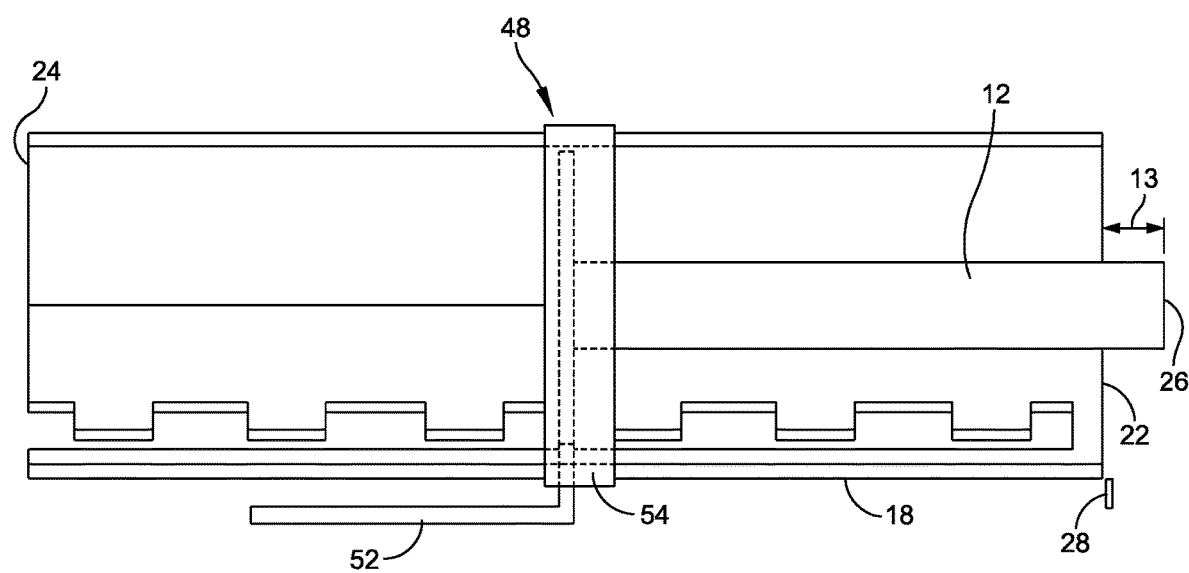
FIG. 4 illustrates a top plan view of the jig system of FIG. 1.
Figure 5:
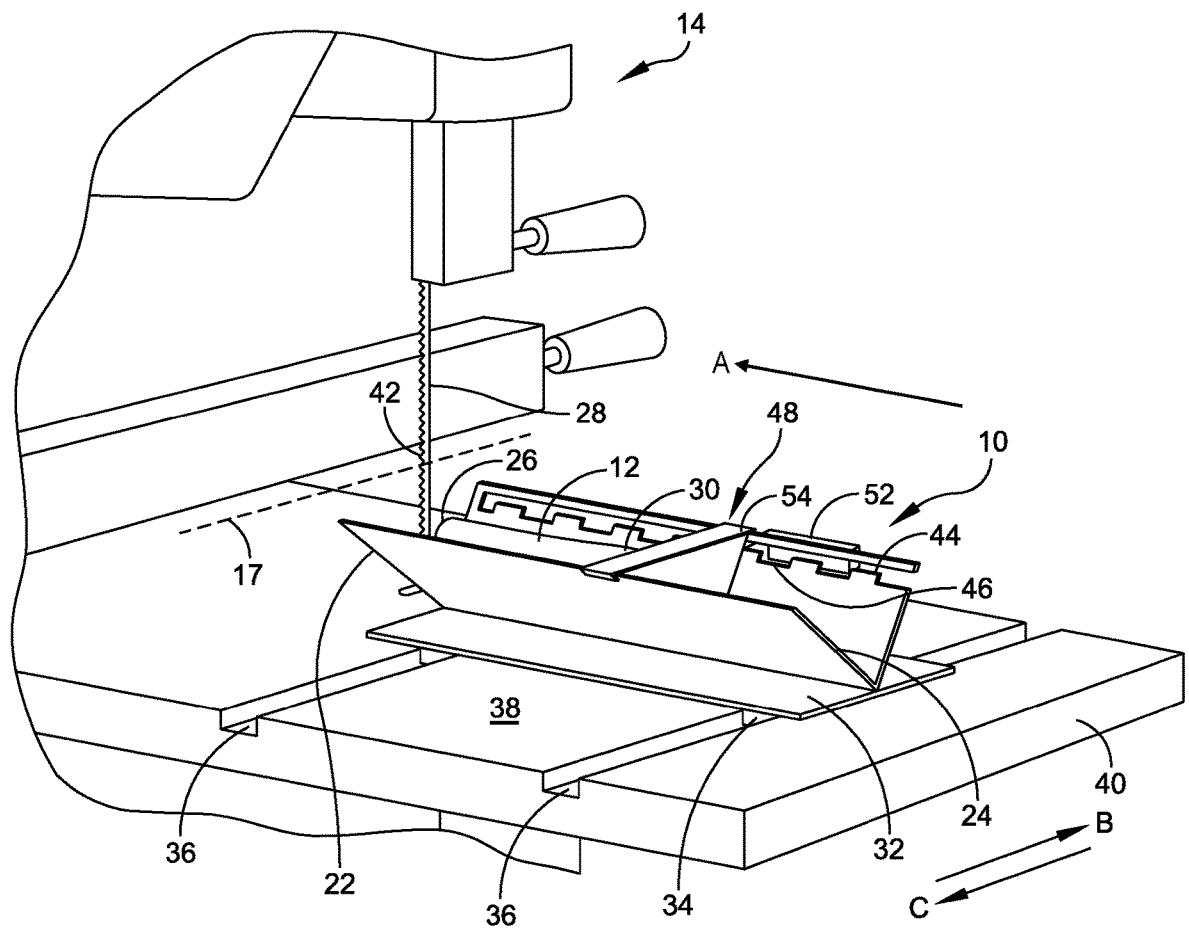
FIG. 5 illustrates a perspective view of the jig system of FIG. 1, as installed upon and in use with an exemplary band saw.

FIGS. 1-4 illustrate respective perspective, side, end, and top-plan views of one embodiment of a jig system 10 for cutting one or more cadaveric bone segments into a number of dimensionally standardized pieces (e.g., strips, shafts, rings, segments, or bone disks), each having predefined specifications or dimensions. FIG. 5 illustrates a perspective view of the jig system 10 installed upon and used in conjunction with an exemplary cutting apparatus, or a band saw 14.

In this embodiment, the jig system 10 may include a v-shaped trough 16 having first and second longitudinal walls 18, 20 and proximal and distal ends 22, 24. When fully assembled, an unprocessed cadaveric long bone 12 such as a femur, tibia, humerus, ulna, radius, and/or fibula may be placed into the v-shaped trough 16. As shown in FIG. 5, the proximal end 22 of the trough 16 may be positioned adjacent to a cutting surface 28, such as, for example, a band saw blade. The bone 12 may be placed such that a proximal end 26 of the bone is located toward/at the proximal end 22 of the trough 16, adjacent to and in a cutting path 17 of the cutting surface 28, and a distal end 30 of the bone 12 is located opposite the cutting surface 28, as discussed below.

The v-shaped trough 16 may be disposed upon and affixed to a plate 32, which may, in turn, ride upon one or more rails 34 that are configured to fit within and glide along a groove or grooves 36 formed within a top surface/overlay 38 of a table 40 of the band saw 14 and parallel to the cutting surface 28 and the cutting path 17 of the cutting surface 28, as shown in FIG. 5. By manually maneuvering or gliding the trough 16 along the groove(s) 36, via the rail(s) 34, a user may introduce an incremental protruding portion 13 (FIG. 4) of the proximal end 26 of the long bone 12 to a cutting edge 42 of the cutting surface/band saw blade 28 to produce a desired cut in the bone 12.

To control a length of the protruding portion 13 of the bone 12 extending from the trough 16, and thus a length from the proximal end 26 of the bone 12 to the cut, to a predefined or standardized dimension, the first longitudinal wall 18 of the v-shaped trough 16 may include a channel 44 having a series of notches or incremental stops 46 extending downward therefrom. A bone-advancement wedge 48 may be placed within the trough 16 and positioned such that an advancement panel 50 of the wedge contacts or abuts the walls 18, 20 of the trough 16 as well as the distal end 30 of the bone placed within the trough 16, as shown in FIG. 4. The bone-advancement wedge 48 may also feature a handle 52 that extends through the channel 44 formed in the trough 16. The handle 52 may be configured to selectively engage with each of the incremental stops 46 at the user's discretion. Thus, in operation, the user may set the handle 52 into the proper incremental stop 46 to push a desired incremental protruding portion 13 of bone 12 from the proximal end 22 of the trough 16 and affect a desired length of the resulting cut.

In operation, and as shown in FIG. 5, by advancing the wedge 48 toward the proximal end 22 of the trough 16 in the direction of arrow A, and by sliding the rails 34 of system 10 back and forth in the directions of arrows B and C along the groove(s) 36 in the band saw table 40 parallel to the band saw blade 28, as described above, the user may introduce the protruding portion 13 of the proximal end 26 of the long bone 12 to the cutting edge 42 of the blade 28. The operator may incrementally repeat the step of advancing the handle 52 into the next incremental stop 46 and then passing the system 10, and thus the bone 12, across the blade to cut the entire bone shaft into standardized pieces.

While the system may be used to cut a long bone shaft into bone disks or rings, it may also be used to create cortical segments following initial bone shaft processing involving cutting long bone shafts into longitudinal strips along a longitudinal axis of the bone. These strips are generally not uniform or square in profile and thus do not lay flat. When manually passed through a band saw blade individually, the irregularities and lack of symmetrical or square nature often cause the bone strips to shift suddenly during cutting operations, jeopardizing cutting accuracy and risking dislodgement of the bone strip.

Figure 6:
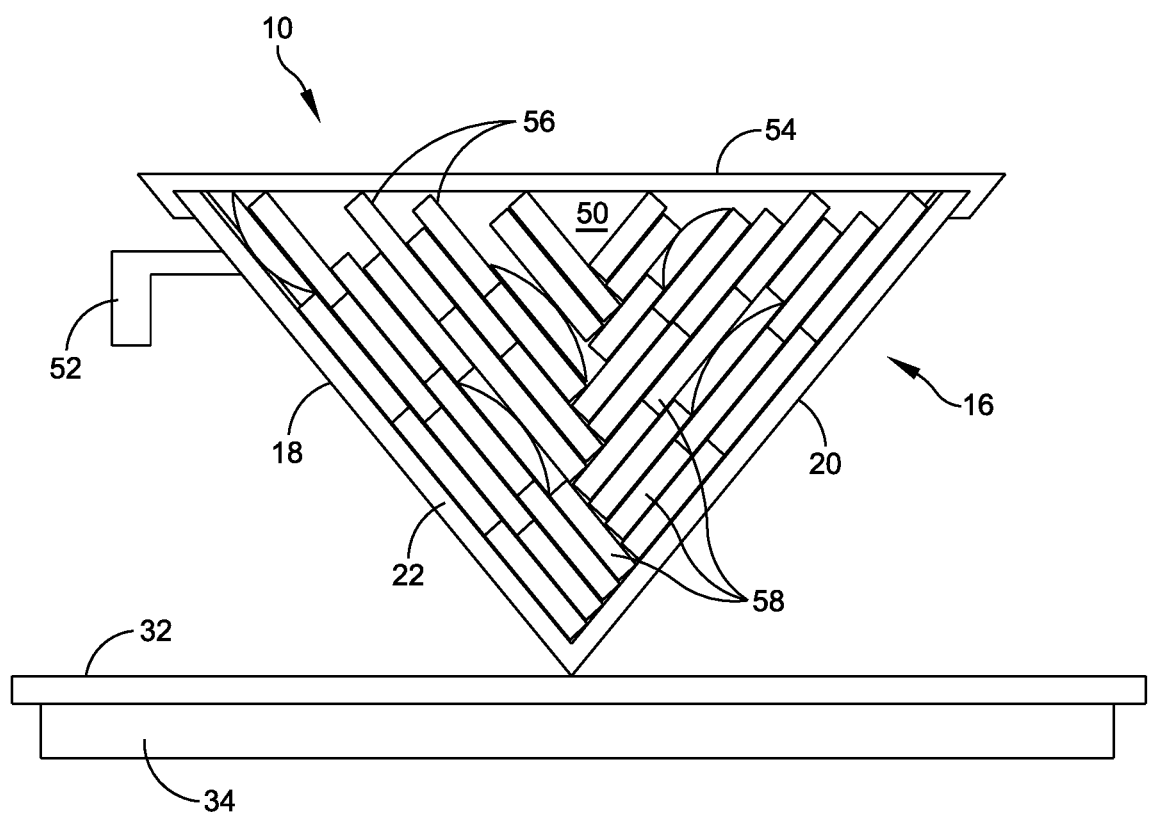
FIG. 6 illustrates a front-end view of the jig system of FIG. 1 supporting a number of pre-processed, cortical bone strips for safely cutting into dimensionally standardized pieces.
Figure 7:
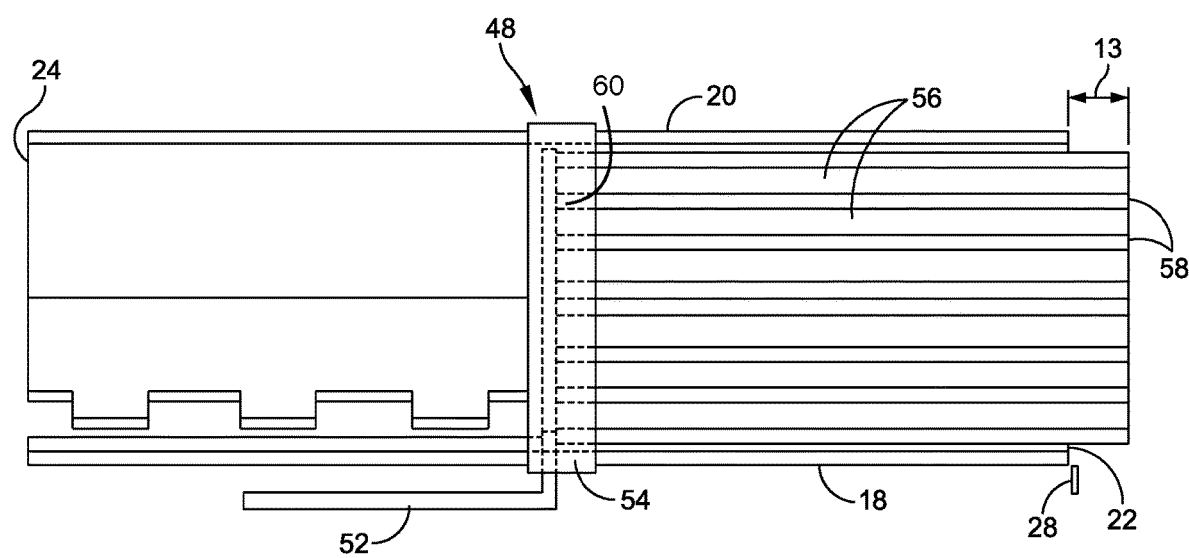
FIG. 7 illustrates a top plan view of the jig system of FIG. 6 supporting the pre-processed, cortical bone strips.

To address this unique problem, one embodiment of the bone-advancement wedge may also include a compression lip 54 that extends outward from a top portion of the advancement panel 50 toward the proximal end 22 of the trough 16. As shown in FIGS. 6-7, an operator may place several longitudinal bones 12 or strips 56 into the v-shaped trough 16. In this position, a downward force of the moving blade 28 tethers a collective proximal or leading edge 58 of the bone strips 56 in place, while the compression lip 54 of the bone-advancement wedge 48 simultaneously secures a collective distal or trailing end 60 of the bone strips 56 in place. As a result, multiple longitudinal strips 56 may be cut into standardized segments at one time, thereby increasing user safety as well as increasing preparation efficiency and operational productivity. The compression lip 54 may be vertically adjustable to accommodate a varying number of bone strips 56 within the v-shaped trough 16. Alternately, the system 10 may include a number of interchangeable bone-advancement wedges 48, each having a compression lip 54 extending proximally from the advancement panel 50 at a different height to accommodate varying numbers/heights of long bones 12 or bone strips 56 placed within the v-shaped trough 16.

Figure 8:
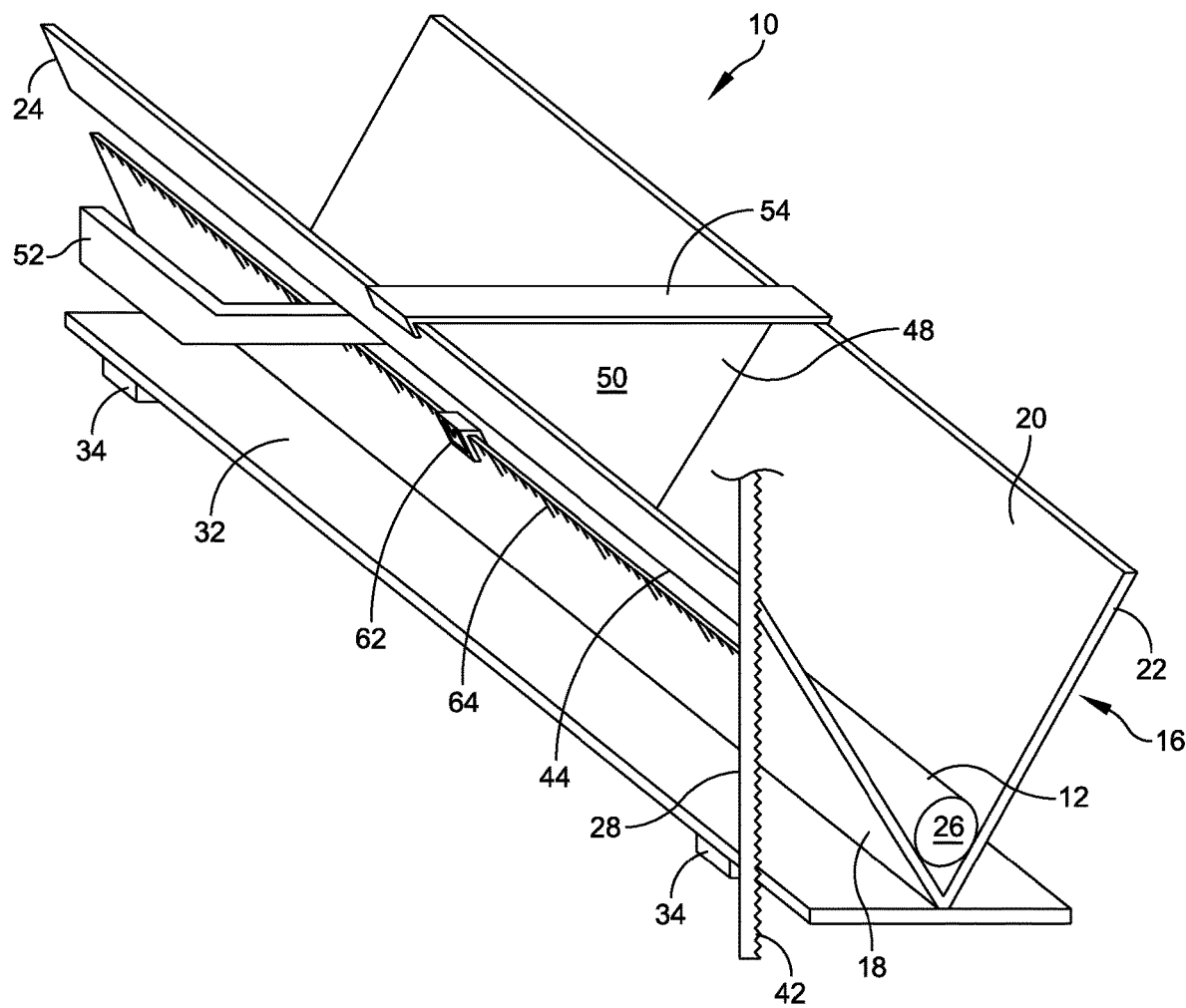
FIG. 8 illustrates a perspective view of one embodiment of a bone-cutting jig system featuring an adjustable slider and measurement gauge for customizing a number of incremental cutting stops.
Figure 9:
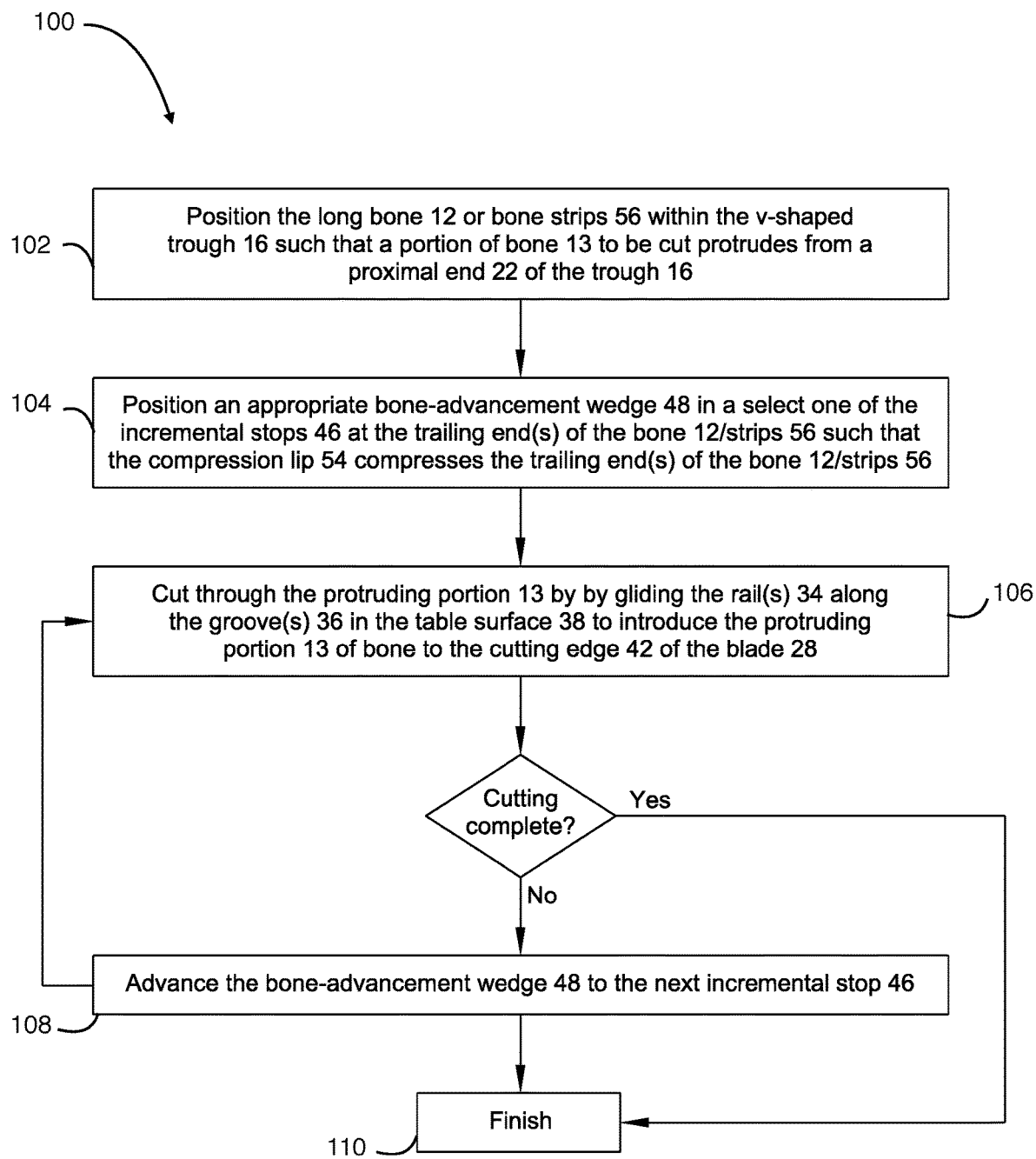
FIG. 9 provides a flowchart depicting an exemplary method of cutting one or more long bones or cortical bone strips into dimensionally standardized pieces using the jig system of FIG. 1 or 6.

In one embodiment shown in FIG. 8, the incremental stops formed in the channel 44 of the trough 16 may incorporate or be formed by an adjustable, settable slider 62 and a measurement gauge 64 that allow the stop lengths to be manually varied, either uniformly or individually, depending on the length of cuts desired. The adjustable slider 62 may attach along the measurement gauge 64 via a frictional fit or via any other appropriate mechanism that provides both adjustability to and securement at the desired increment along the measurement gauge 64 between the proximal and the distal ends 22, 24 of the trough 16. Embodiments of the jig may also incorporate a settable bevel gauge or another appropriate angle-measurement and setting mechanism that allows the operator to measure or set an angle of the table/overlay 38 supporting the jig 10, the jig 10 itself, or the bone 12/bone strips 56 in order to affect compound cuts to the bone 12 or the bone strips 56.

The components of the jig system, including the trough, plate, rail(s), and bone-advancement wedge may be formed of surgical stainless steel to accommodate regular sterilization via autoclave. Alternatively, the system components may be constructed of autoclavable plastics such as, for example, high-impact polyvinyl chloride (PVC), polypropylene (PP), polysulfone (PS), polyetheretherketone (PEEK), polymethylpentene (PMP), polycarbonate (PC), PTFE Resin, and/or polymethyl methacrylate (PMMA).

FIG. 8 provides a flowchart depicting an exemplary method (100) of cutting a bone segment 12 or a number of bone strips 56 using an embodiment of the jig system 10 described above. To begin, the operator may place a long bone 12 or a number of bone strips 56 within the v-shaped trough 16 (102) before positioning the appropriate bone-advancement wedge 48 within the v-shaped trough 16 such that the advancement panel 50 is in contact with the distal end(s) of the bone 12 or the strips 56, the compression lip 54 is positioned above the bone 12/strips 56 such that it compresses the bone 12 or strips 56 downward into the trough 16, and the handle 52 is engaged with a desired one of the incremental stops 46 (104). The user may then introduce the protruding portion 13 of the bone to the blade 28 by gliding the rail(s) 34 disposed below the trough 16 and the plate 32 along the corresponding groove(s) 36 formed within the band saw table/overlay 38 in a manner that introduces the proximal end(s) 26 of the bone shaft 12 or the strips 56 to the cutting edge 42 of the blade 28, thereby making a desired cut in the bone(s) (106). Once the cut has been made, the user may advance the bone-advancement wedge 48 to the next incremental stop 46 (108). These steps introducing the protruding portion 13 to the cutting edge 42 (106) and advancing the wedge 48 (108) may be repeated until the bone 12/bone strips 56 is/are completely cut into desired pieces having standardized and/or predefined dimensions, while maintaining the user's hands and fingers at a safe distance from the blade. When the cutting operation is complete (110), the system may be sterilized in an autoclave in preparation for another operation.

The process allows for precision bone cuts with little waste, maximizing the gift of tissue donation, which is accomplished in a safe manner that allows operators to maintain an effective barrier between and a safe distance from the cutting edge or abrasive surface, which reduces the potential for traumatic injury caused by exposure to sharp edges, as well as musculoskeletal disorders caused by repetitive hand/wrist/arm motions. The process also increases operational efficiency and overall productivity by allowing for multiple, uniform cuts to be made in multiple bone strips simultaneously.

While the jig system is described in connection with cutting osseous tissue, the system may be used as an aid in cutting other non-square, non-uniform, and/or irregularly-shaped materials as part of other manufacturing operations (e.g., cutting wood, plastic, metal, and/or odd-shaped materials and/or objects).

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A system for cutting one or more cadaveric bone segments into dimensionally standardized pieces using a cutting apparatus having a cutting surface disposed orthogonally to a table, comprising:
   a v-shaped trough extending from a proximal end positioned adjacent a cutting surface to a distal end positioned opposite the cutting surface, the v-shaped trough configured to glide along a top surface of the table parallel to a cutting path defined through the cutting surface, the cutting path extending adjacent the proximal end of the trough, the v-shaped trough forming a number of incremental stops between the proximal end and the distal end; and
   a bone-advancement wedge, the bone-advancement wedge comprising a handle coupled to an advancement panel positioned within the v-shaped trough, wherein when the one or more of the cadaveric bone segments are disposed within the v-shaped trough, proximally advancing the bone-advancement wedge to a next one of the number of the incremental stops proximally advances the one or more of the cadaveric bone segments an incremental distance beyond the cutting path.

2. The system of claim 1, the bone-advancement wedge further comprising a compression lip extending from the advancement panel toward the proximal end of the v-shaped trough, the compression lip configured to secure a distal end of the one or more of the cadaveric bone segments within the v-shaped trough.

3. The system of claim 2, wherein the compression lip has an adjustable height relative to first and second longitudinal walls of the v-shaped trough disposed above a plate.

4. The system of claim 1, wherein the v-shaped trough comprises first and second longitudinal walls disposed above and in attachment to a plate, the plate disposed above and in attachment to at least one rail configured to glide within at least one corresponding groove formed in the table of the cutting apparatus, wherein gliding of the at least one rail within the at least one corresponding groove causes the v-shaped trough to glide along a top surface of the table.

5. The system of claim 4, wherein the number of the incremental stops comprise a number of incremental notches extending in a downward direction toward the plate from a channel formed in the first longitudinal wall.

6. The system of claim 4, wherein the number of the incremental stops comprise an adjustable slider configured for selective adjustment and selective fixation at a desired increment along a measurement gauge formed in the first longitudinal wall, wherein the bone-advancement wedge is manually varied relative to the desired increment along the measurement gauge indicated by the adjustable slider.

7. The system of claim 1, wherein the cutting apparatus comprises a band saw, and wherein the cutting surface comprises a band-saw blade.

8. A jig system for cutting at least one bone segment having a proximal end and a distal end into a number of dimensionally standardized pieces, the jig system comprising:
   at least one rail configured to glide within a groove formed in a band saw table;
   a plate attached to a top surface of the at least one rail;
   a trough attached to a top surface of the plate, the trough having a proximal end disposed adjacent a blade positioned orthogonally to the band saw table, a distal end disposed opposite the blade, first and second longitudinal walls extending between the proximal and the distal ends of the trough, and one or more incremental stops located between the proximal and the distal ends of the trough, the trough configured to receive the at least one bone segment with the proximal end of the at least one bone segment positioned at the proximal end of the trough; and
   a bone-advancement wedge, comprising:
      an advancement panel abutting the distal end of the at least one bone segment, the advancement panel configured to advance to each of the one or more of the incremental stops toward the proximal end of the trough; and
      a handle extending from the advancement panel through the first longitudinal wall of the trough, the handle configured to selectively engage with each of the one or more of the incremental stops, such that when the handle is advanced proximally between the one or more of the incremental stops, the proximal end of the at least one bone segment advances an incremental distance beyond the proximal end of the trough.

9. The jig system of claim 8, the bone-advancement wedge further comprising a compression lip extending proximally from the advancement panel, the compression lip configured to compress the distal end of the at least one bone segment against the first and the second longitudinal walls of the trough.

10. The jig system of claim 9, wherein the compression lip extends proximally from a top portion of the advancement panel.

11. The jig system of claim 9, wherein the at least one rail, the plate, the trough, and the bone-advancement wedge are formed of surgical stainless steel or autoclavable plastic.

12. The jig system of claim 8, wherein the first and the second longitudinal walls form a v shape.

13. The jig system of claim 8, wherein the first longitudinal wall comprises a longitudinal channel, and the one or more of the incremental stops comprise notches extending downward from the longitudinal channel.

14. The jig system of claim 8, wherein a location, between the proximal and the distal ends of the trough, of each of the one or more of the incremental stops is adjustable.

15. The jig system of claim 8, wherein the one or more of the bone segments comprises a long bone or a number of cortical bone strips.

* * * * *